(12) United States Patent
Burgess et al.

(10) Patent No.: US 6,465,493 B1
(45) Date of Patent: Oct. 15, 2002

(54) TRIARYLIMIDAZOLES

(75) Inventors: Joelle L. Burgess; James F. Callahan, both of Collegeville, PA (US)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/958,639

(22) PCT Filed: Apr. 6, 2000

(86) PCT No.: PCT/US00/09147

§ 371 (c)(1),
(2), (4) Date: Oct. 9, 2001

(87) PCT Pub. No.: WO00/61576

PCT Pub. Date: Oct. 19, 2000

Related U.S. Application Data

(60) Provisional application No. 60/128,687, filed on Apr. 9, 1999.

(51) Int. Cl.[7] .................. A61K 31/44; C07D 401/02
(52) U.S. Cl. .................. 514/341; 514/277; 514/340; 514/342; 514/357; 546/269.7; 546/271.4; 546/272.7; 546/276.4; 546/280.4; 546/283.4; 546/329; 546/339
(58) Field of Search .................. 514/277, 357, 514/340, 341, 342; 546/269.7, 271.4, 272.7, 276.4, 280.4, 283.4, 329, 339

(56) References Cited

U.S. PATENT DOCUMENTS 5,656,644 A   8/1997   Adams .................. 514/341
5,776,954 A   7/1998   De Laszlo et al. .......... 514/340

FOREIGN PATENT DOCUMENTS

| GB | 1 381 01 | 1/1975 |
|----|----------|--------|
| WO | WO 95 13067 A | 5/1995 |
| WO | WO 98 22109 A | 5/1998 |

OTHER PUBLICATIONS

Chemical Abstracts, vol. 131, No. 7, 1999 Columbus Ohio, Abstract No. 87659s, p. 641 (XP002146305).

*Primary Examiner*—Zinna Northington Davis
(74) *Attorney, Agent, or Firm*—Nora Stein-Fernandez; Stephen A. Venetianer; Charles M. Kinzig

(57) ABSTRACT

Compounds of formula (I) or a pharmaceutically acceptable salt thereof:

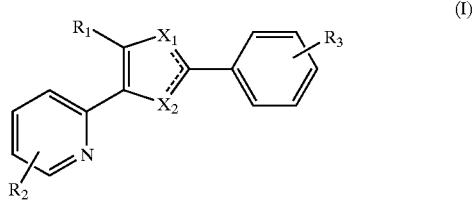

wherein $R_1$, $R_2$ and $R_3$ are various substituent groups; and one of $X_1$ and $X_2$ is N or CR', and the other is NR' or CHR' wherein R' is hydrogen, OH, $C_{1-6}$alkyl, or $C_{3-7}$cycloalkyl; or when one of $X_1$ and $X_2$ is N or CR' then the other may be S or O;
and their use as pharmaceuticals.

12 Claims, No Drawings

TRIARYLIMIDAZOLES

This application is a 371 of PCT/US00/09147 filed Apr. 6, 2000, which claims the benefit of priority to provisional application 60/128,687 filed Apr. 9, 1999.

This invention relates to pyridyl substituted triarylimidazoles which are inhibitors of the transforming growth factor, ("TGF")-β signaling pathway, in particular, the phosphorylation of smad2 or smad3 by the type I or activin-like kinase ("ALK")-5 receptor, methods for their preparation and their use in medicine, specifically in the treatment and prevention of a disease state mediated by this pathway.

TGF-β1 is the prototypic member of a family of cytokines including the TGF-βs, activins, inhibins, bone morphogenetic proteins and Müllerian-inhibiting substance, that signal through a family of single transmembrane serine/threonine kinase receptors. These receptors can be divided in two classes, the type I or activin like kinase (ALK) receptors and type II receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that TGF-β signaling requires both the ALK and type II receptors. Specifically, the type II receptor phosphorylates the GS domain of the type I receptor for TGF-β, ALK5, in the presence of TGF-β. The ALK5, in turn, phosphorylates the cytoplasmic proteins smad2 and smad3 at two carboxy terminal serines. Generally it is believed that in many species, the type II receptors regulate cell proliferation and the type I receptors regulate matrix production. Therefore, preferred compounds of this invention are selective in that they inhibit the type I receptor and thus matrix production, and not the type I receptor mediated proliferation.

Activation of the TGF-β1 axis and expansion of extracellular matrix are early and persistent contributors to the development and progression of chronic renal disease and vascular disease. Border W. A., Noble N. A., *N. Engl. J. Med.*, Nov. 10, 1994; 331(19):1286–92. Further, TGF-β1 plays a role in the formation of fibronectin and plasminogen activator inhibitor-1, components of sclerotic deposits, through the action of smad3 phosphorylation by the TGF-β1 receptor ALK5. Zhang Y., Feng X. H., Derynck R., *Nature*, Aug. 27, 1998; 394(6696):909–13; Usui T., Takase M., Kaji Y., Suzuki K., Ishida K., Tsuru T., Miyata K., Kawabata M., Yamashita H., *Invest. Ophthalmol. Vis. Sci.*, October 1998; 39(11): 1981–9.

Progressive fibrosis in the kidney and cardiovascular system is a major cause of suffering and death and an important contributor to the cost of health care. TGF-β1 has been implicated in many renal fibrotic disorders. Border W. A., Noble N. A., *N. Engl. J. Med.*, Nov 10, 1994; 331(19) :1286–92. TGF-β1 is elevated in acute and chronic glomerulonephritis, Yoshioka K., Takemura T., Murakami K., Okada M., Hino S., Miyamoto H., Maki S., *Lab. Invest.*, February 1993; 68(2):154–63, diabetic nephropathy, Yamamoto, T., Nakamura, T., Noble, N. A., Ruoslahti, E., Border, W. A., (1993) *PNAS* 90:1814–1818, allograft rejection, HIV nephropathy and angiotensin-induced nephropathy, Border W. A., Noble N. A., *N. Engl. J. Med.*, Nov. 10, 1994; 331(19):1286–92. In these diseases the levels of TGF-β1 expression coincide with the production of extracellular matrix. Three lines of evidence suggest a causal relationship between TGF-β1 and the production of matrix. First, normal glomeruli, mesangial cells and non-renal cells can be induced to produce extracellular-matrix protein and inhibit protease activity by exogenous TGF-β1 in vitro. Second, neutralizing anti-bodies against TGF-β1 can prevent the accumulation of extracellular matrix in nephritic rats. Third, TGF-β1 transgenic mice or in vivo transfection of the TGF-β1 gene into normal rat kidneys resulted in the rapid development of glomerulosclerosis. Kopp J. B., Factor V. M., Mozes M., Nagy P., Sanderson N., Bottinger E. P., Klotman P. E., Thorgeirsson S. S., *Lab Invest*, June 1996; 74(6):991–1003. Thus, inhibition of TGF-β1 activity is indicated as a therapeutic intervention in chronic renal disease.

TGF-β1 and its receptors are increased in injured blood vessels and are indicated in neointima formation following balloon angioplasty, Saltis J., Agrotis A., Bobik A., *Clin Exp Pharmacol Physiol*, March 1996; 23(3):193–200. In addition TGF-β1 is a potent stimulator of smooth muscle cell ("SMC") migration in vitro and migration of SMC in the arterial wall is a contributing factor in the pathogenesis of atherosclerosis and restenosis. Moreover, in multivariate analysis of the endothelial cell products against total cholesterol, TGF-β receptor ALK5 correlated with total cholesterol (P<0.001) Blann A. D., Wang J. M., Wilson P. B., Kumar S., *Atherosclerosis*, February 1996; 120(1–2):221–6. Furthermore, SMC derived from human atherosclerotic lesions have an increased ALK5/TGF-β type II receptor ratio. Because TGF-β1 is over-expressed in fibroproliferative vascular lesions, receptor-variant cells would be allowed to grow in a slow, but uncontrolled fashion, while overproducing extracellular matrix components McCaffrey T. A., Consigli S., Du B., Falcone D. J., Sanborn T. A., Spokojny A. M., Bush H. L., Jr., *J Clin Invest*, December 1995; 96(6):2667–75. TGF-β1 was immunolocalized to non-foamy macrophages in atherosclerotic lesions where active matrix synthesis occurs, suggesting that non-foamy macrophages may participate in modulating matrix gene expression in atherosclerotic remodeling via a TGF-β-dependent mechanism. Therefore, inhibiting the action of TGF-β1 on ALK5 is also indicated in atherosclerosis and restenosis.

TGF-β is also implicated in peritoneal adhesions Saed G. M., Zhang W., Chegini N., Holmdahl L., and Diamond M P., *Wound Repair Regeneration*. 7(6):504–510, 1999 November–December. Therefore, inhibitors of ALK5 would be beneficial in preventing peritoneal and sub-dermal fibrotic adhesions following surgical procedures.

Surprisingly, it has now been discovered that a class of 2-pyridyl substituted triarylimidazoles of formula (I), function as potent and selective non-peptide inhibitors of ALK5 kinase and therefore, have utility in the treatment and prevention of various disease states mediated by ALK5 kinase mechanisms, such as chronic renal disease, acute renal disease, wound healing, arthritis, osteoporosis, kidney disease, congestive heart failure, ulcers, occular disorders, corneal wounds, diabetic nephropathy, impaired neurological function, Alzheimer's disease, trophic conditions, atherosclerosis, peritoneal and sub-dermal adhesion, any disease wherein fibrosis is a major component, including, but not limited to lung fibrosis and liver fibrosis, and restenosis.

According to the invention there is provided a compound of formula (I) or a pharmaceutically acceptable salt thereof:

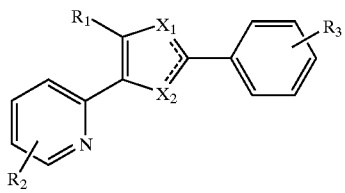

(I)

wherein $R_1$ is naphthyl, anthracenyl, or phenyl optionally substituted with one or more substituents selected from the group consisting of halo, $C_{1-6}$alkoxy, $C_{1-6}$alkylthio, $C_{1-6}$alkyl, —O—$(CH_2)_n$—Ph, —S—$(CH_2)_n$—Ph, cyano, phenyl, and $CO_2R$, wherein R is hydrogen or $C_{1-6}$alkyl and n is 0, 1, 2 or 3; or $R_1$ is phenyl fused with an aromatic or non-aromatic cyclic ring of 5–7 members wherein said cyclic ring optionally contains up to two heteroatoms, independently selected from N, O and S;

$R_2$ is H, $NH(CH_2)_n$—Ph or NH—$C_{1-6}$alkyl, wherein n is 0, 1, 2 or 3;

$R_3$ is $CO_2H$, $CONH_2$, CN, $NO_2$, $C_{1-6}$alkylthio, —$SO_2$—$C_{1-6}$alkyl, $C_{1-6}$alkoxy, $SONH_2$, CONHOH, $NH_2$, CHO, $CH_2OH$, $CH_2NH_2$, or $CO_2R$, wherein R is hydrogen or $C_{1-6}$alkyl; and one of $X_1$ and $X_2$ is N or CR', and the other is NR' or CHR' wherein R' is hydrogen, OH, $C_{1-6}$alkyl, or $C_{3-7}$cycloalkyl; or when one of $X_1$ and $X_2$ is N or CR' then the other may be S or O.

As used herein, the double bond indicated by the dotted lines of formula (I), represent the possible tautomeric ring forms of the compounds falling within the scope of this invention. It will be understood that when one of $X_1$ and $X_2$ is carbon and the other is nitrogen, then the double bond could be either to the carbon or the nitrogen. When $X_1$ and $X_2$ are both carbon, then the double bond could be to either $X_1$ or $X_2$. When $X_1$ and $X_2$ are both nitrogen, then the double bond is to the unsubstituted nitrogen.

Preferably $R_1$ is optionally substituted naphthyl or phenyl. More preferably $R_1$ is phenyl optionally substituted with one or more substituents selected from the group consisting of halo, $C_{1-6}$alkoxy, $C_{1-6}$alkylthio, and phenyl; or $R_1$ is phenyl fused with an aromatic or non-aromatic cyclic ring of 5–7 members wherein said cyclic ring optionally contains up to two heteroatoms, independently selected from N, O and S, for example $R_1$ represents benzo[1,3]dioxolyl, 2,3-dihydrobenzo[1,4]dioxinyl, benzoxazolyl, benzothiazolyl, benzo[1,2,5]oxadiazolyl, benzo[1,2,5]thiadiazolyl or dihydrobenzofuranyl.

Preferably, $R_2$ is positioned ortho to the nitrogen of the pyridyl ring. More preferably $R_2$ is hydrogen.

Preferably $R_3$ is $CO_2H$, $CONH_2$, CN, $NO_2$, $SONH_2$, CONHOH, $NH_2$, CHO, $CH_2OH$ or $CH_2NH_2$.

Preferably one of $X_1$ and $X_2$ is N or CR', and the other is NR' or CHR' wherein R' is hydrogen, $C_{1-6}$alkyl, or $C_{3-7}$cycloalkyl, provided that at least one of $X_1$ and $X_2$ is N or NR'; or one of $X_1$ and $X_2$ is N and the other is O. More preferably one of $X_1$ and $X_2$ is N and the other is NR'.

Preferably each R' is hydrogen.

Specific compounds of the invention which may be mentioned include the following and pharmaceutically acceptable salts thereof:

4-[4-(4-Fluorophenyl)-5-(2-pyridyl)-1-hydroxy-1H-imidazol-2-yl]benzonitrile;
4-[4-(4-Fluorophenyl)-5-(2-pyridyl)-1H-imidazol-2-yl] benzonitrile;
4-[4-(4-Fluorophenyl)-5-(2-pyridyl)-1H-imidazol-2-yl] benzoic acid;
Methyl 4-[4-(4-fluorophenyl)-5-(2-pyridyl)-1H-imidazol-2-yl]benzoate;
Ethyl 4-[4-(4-fluorophenyl)-5-(2-pyridyl)-1H-imidazol-2-yl]benzoate
4-(4-Benzo[1,3]dioxol-5-yl-1-hydroxy-5-pyridin-2-yl-1H-imidazol-2-yl)benzonitrile
4-(4-Benzo[1,3]dioxol-5-yl-5-pyridin-2-yl-1H-imidazol-2-yl)benzonitrile;
4-(4-Benzo[1,3]dioxol-5-yl-5-pyridin-2-yl-1H-imidazol-2-yl)benzoic acid;
2-[4-Benzo[1,3]dioxol-5-yl-2-(4-nitrophenyl)-1H-imidazol-5-yl]pyridine;
3-(4-Benzo[1,3]dioxol-5-yl-5-pyridin-2-yl-1H-imidazol-2-yl)phenylamine;
4-[4-(4-Fluorophenyl)-2-(4-nitrophenyl)-1H-imidazol-5-yl]pyridine;
4-[4-(4-Fluorophenyl)-5-pyridin-2-yl-1H-imidazol-2-yl) phenylamine
4-(4-Benzo[1,3]dioxol-5-yl-5-pyridin-2-yl-1H-imidazol-2-yl)phenyl]methanol;
4-(4-Benzo[1,3]dioxol-5-yl-5-pyridin-2-yl-1H-imidazol-2-yl)benzamide;
4-[4-(2,3-Dihydro-benzo[1,4]dioxin-6-yl)-5-pyridin-2-yl-1H-imidazol-2-yl]-benzonitrile;
4-[4-(2,3-Dihydro-benzo[1,4]dioxin-6-yl)-5-pyridin-2-yl-1H-imidazol-2-yl]benzamide;
4-[4-(2,3-Dihydro-benzofuran-5-yl)-5-pyridin-2-yl-1H-imidazol-2-yl]benzamide;
3-[4-Benzo[1,3]dioxol-5-yl-5-pyridin-2-yl-1H-imidazol-2-yl)benzonitrile;
4-[4-(2,3-Dihydro-benzofuran-6-yl)-5-pyridin-2-yl-1H-imidazol-2-yl]benzonitrile;
4-[4-(2,3-Dihydro-benzofuran-6-yl)-5-pyridin-2-yl-1H-imidazol-2-yl]benzamide;
3-(4-Benzo[1,3]dioxol-5-yl-5-pyridin-2-yl-1H-imidazol-2-yl)benzoic acid;
4-[4-(4-Methoxyphenyl)-5-(2-pyridyl)-1H-imidazol-2yl] benzonitrile;
4-[4-(2,2-Difluoro-benzo[1,3]dioxol-5-yl)-5-pyridin-2-yl-1H-imidazol-2-yl]benzamide;
4-[4-(2,3-Dihydro-benzo[1,4]dioxin-6-yl)-1-methyl-5-pyridin-2-yl-1H-imidazol-2-yl]benzamide;
4-[5-(2,3-Dihydro-benzo[1,4]dioxin-6-yl)-1-methyl-4-pyridin-2-yl-1H-imidazol-2-yl]benzamide;
4-(5-Benzo[1,3]dioxol-5-yl-4-pyridin-2-yl-oxazol-2-yl) benzonitrile;
4-(5-Benzo[1,3]dioxol-5-yl-4-pyridin-2-yl-oxazol-2-yl) benzamide; and
4-(4-Benzo[1,3]dioxol-5-yl-5-pyridin-2-yl-1H-pyrrol-2-yl)benzamide.

Suitable, pharmaceutically acceptable salts of the compounds of formula (I) include, but are not limited to, salts with inorganic acids such as hydrochloride, sulfate, phosphate, diphosphate, hydrobromide, and nitrate, or salts with an organic acid such as malate, maleate, fumarate, tartrate, succinate, citrate, acetate, lactate, methanesulfonate, p-toluenesulfonate, palmitate, salicylate, and stearate.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably at least 10% of a compound of the formula (I) or pharmaceutically acceptable derivative thereof.

The term "$C_{1-6}$alkyl" as used herein whether on its own or as part of a larger group e.g. $C_{1-6}$alkoxy, means a straight or branched chain radical of 1 to 6 carbon atoms, including, but not limited to methyl, ethyl, n-propyl, isopropyl, n-butyl, sec-butyl, isobutyl and tert-butyl.

$C_{1-6}$ haloalkyl groups may contain one or more halo atoms, a particular $C_{1-6}$ haloalkyl group that may be mentioned in $CF_3$.

The terms "halo" or "halogen" are used interchangeably herein to mean radicals derived from the elements chlorine, fluorine, iodine and bromine.

The term "$C_{3-7}$cycloalkyl" as used herein means cyclic radicals of 3 to 7 carbons, including but not limited to cyclopropyl, cyclopentyl and cyclohexyl.

The term "aryl" as used herein means 5- to 14-membered substituted or unsubstituted aromatic ring(s) or ring systems which may include bi- or tri-cyclic systems, including, but not limited to phenyl and naphthyl.

The term "ALK5 inhibitor" as used herein means a compound, other than inhibitory smads, e.g. smad6 and smad7, which selectively inhibits the ALK5 receptor preferentially over p38 or type II receptors.

The term "ALK5 mediated disease state" as used herein means any disease state which is mediated (or modulated) by ALK5, for example a disease which is modulated by the inhibition of the phosphorylation of smad 2/3 in the TGF-1β signaling pathway.

The term "ulcers" as used herein includes, but is not limited to, diabetic ulcers, chronic ulcers, gastric ulcers, and duodenal ulcers.

The compounds of formula (I) can be prepared by art-recognized procedures from known or commercially available starting materials. If the starting materials are unavailable from a commercial source, their synthesis is described herein, or they can be prepared by procedures known in the art.

Specifically, compounds of formula (I) wherein one of $X_1$ and $X_2$ is N and the other is NH or N—OH may be prepared as illustrated in Scheme 1 for compounds wherein $X_1$ is N and $X_2$ is NH or N—OH. Using the method detailed in U.S. Pat. No. 3,940,486, N-methoxy-N-methylaryl amide is alkylated with the anion generated from a 2(6)-methylpyridine to give a ketone. The ketone is treated with sodium nitrite to form the oxime which is condensed with an aldehyde and $NH_4OAc$ to give a hydroxy imidazole. The hydroxy imidazole may then be reduced with triphenylphosphite by the method described in U.S. Pat. No. 5,656,644 to give the corresponding imidazole.

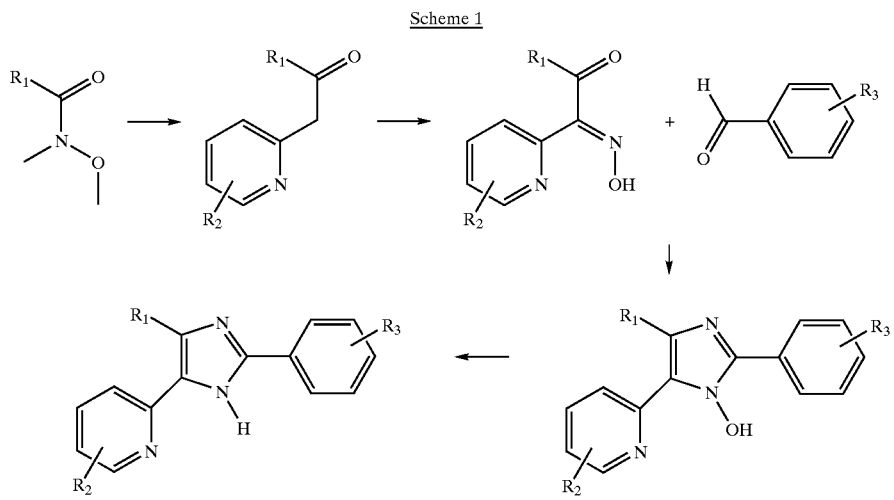

Scheme 1

Alternatively, the ketone may be oxidised to a diketone with HBr in DMSO. This diketone can then be condensed with a suitably substituted benzaldeyde and ammonium acetate to give the imidazole according to the method outlined in WO 98/56788 and as illustrated in Scheme 2 for compounds wherein $X_1$ is N and $X_2$ is NH.

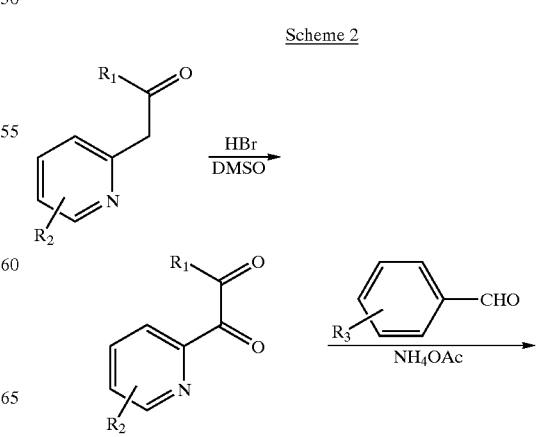

Scheme 2

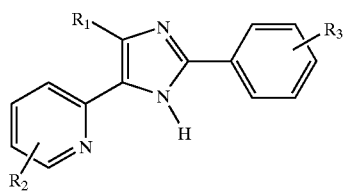

Non-selective alkylation of the imidazole nitrogen (using one of the procedures outlined in N. J. Liverton et al; *J. Med. Chem.*, 1999, 42, 2180–2190) with a compound of formula L—R' wherein L is a leaving group, e.g. halo, sulfonate or triflate, will yield both isomers of the compounds where one of $X_1$ or $X_2$ is NR' wherein R' is $C_{1-6}$alkyl, or $C_{3-7}$cycloalkyl, as illustrated in Scheme 3, the isomers can be separated by chromatographic methods.

Scheme 3

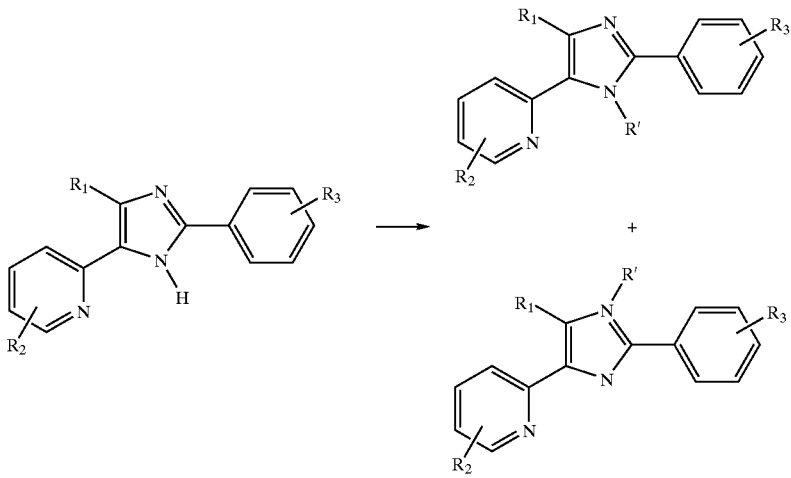

Compounds of formula (I) wherein one of $X_1$ and $X_2$ is N and the other is O may be prepared according to Scheme 4. The oximino ketone may be reduced via catalytic hydrogen to afford the amino ketone which can be further reacted with an appropriately substituted benzoyl chloride compound. Reaction of the amide product with thionyl chloride affords the oxazole product.

Scheme 4

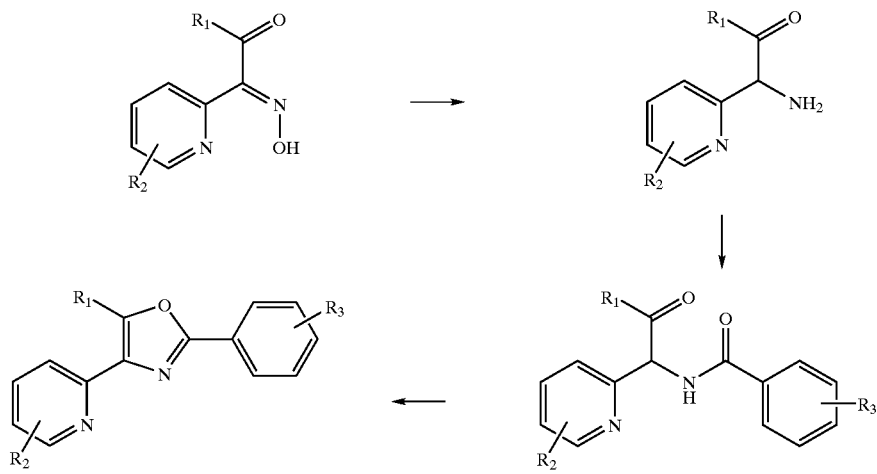

Compounds of formula (I) where one of $X_1$ and $X_2$ is CH or CHR' may be prepared according to Scheme 5. A suitably substituted acetophenone and a benzaldehyde are condensed under basic conditions to afford the enone aldol product. This enone is then reacted with a pyridine-2-carboxaldehyde under sodium cyanide catalysis to afford the 1,4-diketone which is condensed with ammonium acetate to afford the pyrrole.

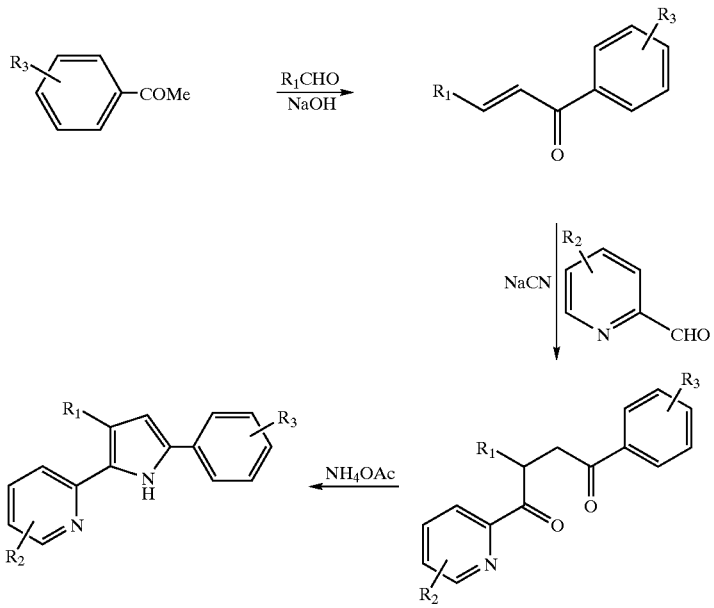

Scheme 5

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

Further details for the preparation of compounds of formula (I) are found in the examples.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable salts thereof.

The invention further provides the use of a compound of formula (I) or a pharmaceutically acceptable salt thereof, in the manufacture of a medicament for the treatment of a disease mediated by the ALK5 receptor in mammals.

The invention further provides a method of treatment of a disease mediated by the ALK5 receptor in mammals, comprising administering to a mammal in need of such treatment, a therapeutically effective amount of a compound of formula (I) or a pharmaceutically acceptable salt thereof.

ALK5-mediated disease states, include, but are not limited to, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, trophic conditions, atherosclerosis, any disease wherein fibrosis is a major component, including, but not limited to peritoneal and sub-dermal adhesion, lung fibrosis and liver fibrosis, and restenosis.

By the term "treating" is meant either prophylactic or therapeutic therapy.

The invention further provides a method of inhibiting the TGF-β signaling pathway in mammals, for example, inhibiting the phosphorylation of smad2 or smad3 by the type I or activin-like kinase ALK5 receptor, which method comprises administering to a mammal in need of such treatment, a therapeutically effective amount of a compound of formula (I) or a pharmaceutically acceptable salt thereof.

The invention further provides the use of a compound of formula (I) or a pharmaceutically acceptable salt thereof, in the manufacture of a medicament for inhibiting the TGF-β signaling pathway in mammals.

The invention further provides a method of inhibiting matrix formation in mammals, for example, by inhibiting the phosphorylation of smad2 or smad3 by the type I or activin-like kinase ALK5 receptor, which method comprises administering to a mammal in need of such treatment, a therapeutically effective amount of a compound of formula (I) or a pharmaceutically acceptable salt thereof.

The invention further provides the use of a compound of formula (I) or a pharmaceutically acceptable salt thereof, in the manufacture of a medicament for inhibiting matrix formation in mammals.

The compounds of formula (I) and pharmaceutically acceptable salts thereof, may be administered in conventional dosage forms prepared by combining a compound of formula (I) with standard pharmaceutical carriers or diluents according to conventional procedures well known in the art.

These procedures may involve mixing, granulating and compressing or dissolving the ingredients as appropriate to the desired preparation.

According to a further aspect of the present invention there is provided a pharmaceutical composition comprising a compound of formula (I), or a pharmaceutically acceptable salt thereof, and a pharmaceutically acceptable carrier or diluent.

The pharmaceutical compositions of the invention may be formulated for administration by any route, and include those in a form adapted for oral, topical or parenteral administration to mammals including humans.

The compositions may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

It will be recognized by one of skill in the art that the optimal quantity and spacing of individual dosages of a compound of formula (I) will be determined by the nature and extent of the condition being treated, the form, route and site of administration, and the particular mammal being treated, and that such optimums can be determined by conventional techniques. It will also be appreciated by one of skill in the art that the optimal course of treatment, i.e. the number of doses of the compound of formula (I) given per day for a defined number of days, can be ascertained by those skilled in the art using conventional course of treatment determination tests.

No toxicological effects are indicated when a compound of formula (I) or a pharmaceutically acceptable salt thereof is administered in the above-mentioned dosage range.

All publications, including, but not limited to, patents and patent applications cited in this specification, are herein incorporated by reference as if each individual publication were specifically and individually indicated to be incorporated by reference herein as though fully set forth.

The following examples are to be construed as merely illustrative and not a limitation on the scope of the invention in any way. In the Examples, unless indicated otherwise, mass spectra were performed using an Hitachi Perkin-Elmer RMU-6E with chemical ionization technique (CI) or a Micromass Platform II instrument with electrospray (ES) ionization technique.

EXAMPLES

Example 1: 4-[4-(4-Fluorophenyl)-5-(2-pyridyl)-1-hydroxy-1H-imidazol-2-yl]benzonitrile The title compound was prepared using the method in U.S. Pat. No. 3,940,486 to prepare 2-(t-butyl)4-(phenyl)-N-1-hydroxy-5-(4-pyridyl)imidazole except using 2-hydroxyimino-2-(2-pyridyl)-(4-fluoro)-acetophenone and 4-cyanobenzaldehyde. ESMS $(M+H)^+$=357.1.

Example 2: 4-[4-(4-Fluorophenyl)-5-(2-pyridyl)-1H-imidazol-2-yl]benzonitrile

The title compound was prepared using the procedure in U.S. Pat. No. 5,656,644 (Example 1) to prepare 2-(4-cyanophenyl)4-(4-fluorophenyl)-5-(4-pyridyl)-1H-imidazole except using 2-(4-cyanophenyl)4-(4-fluorophenyl)-N-1-hydroxy-5-(2-pyridyl)-imidazole. ESMS $(M+H)^+$=341.2.

Example 3: 4-[4-(4-Fluorophenyl)-5-(2-pyridyl)-1H-imidazol-2-yl]benzoic acid The title compound was prepared using the procedure in U.S. Pat. No. 5,656,644 (Example 9) to prepare 4-[4-(4-fluorophenyl)-5-(4-pyridyl)-1H-imidazol-2yl]benzoic acid except using 4-[4-(4-fluorophenyl)-5-(2-pyridyl)-1H-imidazol-2yl]benzonitrile. ESMS (M+H)$^+$=360.1.

Example 4: Methyl 4-[4-(4-fluorophenyl)-5-(2-pyridyl)-imidazol-2-yl]benzoate Material from Example 3 was heated at reflux in a solution of methanol/sulfuric acid for 18 h. The solution was concentrated to remove the methanol and the resulting aqueous solution was extracted with chloroform to yield the title compound. ESMS (M+H)$^+$=374.2.

Example 5: Ethyl 4-[4-(4-fluorophenyl)-5-(2-pyridyl)-imidazol-2-yl]benzoate

Material from Example 3 was heated at reflux in a solution of ethanol/sulfuric acid for 18 h. The solution was concentrated to removed the ethanol and the resulting aqueous solution was extracted with chloroform to yield the title compound. ESMS (M+H)$^+$=388.2.

Example 6: 4-(4-Benzo[1,3]dioxol-5-yl-1-hydroxy-5-pyridin-2-yl-1H-imidazol-2-yl)-benzonitrile The title compound was prepared using the procedure of Example 1 except using 1-benzo[1,3]dioxol-5-yl-2-pyridin-2-ylethane-1,2-dione oxime and 4-cyanobenzaldehyde. ESMS (M+H)$^+$=383.1.

Example 7: 4-(4-Benzo[1,3]dioxol-5-yl-5-pyridin-2-yl-1H-imidazol-2-yl)benzonitrile The title compound was prepared using the procedure of Example 2 except replacing 4-[4-(4-fluorophenyl)-1-hydroxy-5-pyridin-2-yl-1H-imidazol-2-yl]-benzonitrile with 4-(4-benzo[1,3]dioxol-5-yl-1-hydroxy-5-pyridin-2-yl-1H-imidazol-2-yl)-benzonitrile. ESMS (M+H)$^+$=367.1.

Example 8: 4-(4-Benzo[1,3]dioxol-5-yl-5-pyridin-2-yl-1H-imidazol-2-yl)benzoic acid The title compound was prepared using the procedure of Example 3 except replacing 4-[4-(4-fluorophenyl)-5-pyridin-2-yl-1H-imidazol-2-yl9 benzonitrile with 4-(4-benzo[1,3]dioxol-5-yl-5-pyridin-2-yl-1H-imidazol-2-yl) benzonitrile. ESMS (M+H)$^+$=386.1.

Example 9: 2-[4-Benzo[1,3]dioxol-5-yl-2-(4-nitrophenyl)-1H-imidazol-5-yl]pyridine The title compound was prepared using the procedure of Example 1 except using 1-benzo[1,3]dioxol-5-yl-2-pyridin-2-yl-ethane-1,2-dione oxime and 4-nitrobenzaldehyde. $^1$H NMR (250 MHz; CD$_3$OD) δ: 5.71 (2H, s), 6.58 (1H, d), 6.73 (2H, m), 7.03 (1H, m), 7.20–7.35 (1H, m), 7.47 (1H, m), 8.00 (4H, m), 8.31 (1H, m); m/z (ESMS): 372 [M+H].

Example 10: 3-(4-Benzo[1,3]dioxol-5-yl-5-pyridin-2-yl-1H-imidazol-2-yl)phenylamine The title compound was prepared by tin(II)chloride reduction of 2-[4-benzo[1,3]dioxol-5-yl-2-(4-nitrophenyl)-1H-imidazol-5-yl]pyridine (Example 9). m/z (ESMS): 342. [M+H].

Example 11: 4-[4-(4-Fluorophenyl)-2-(4-nitrophenyl)-1H-imidazol-5-yl]pyridine The title compound was prepared using the procedure of Example 1 except using 1-(4-fluorophenyl)-2-pyridin-2-yl-ethane-1,2-dione oxime and 4-nitrobenzaldehyde. m/z (ESMS): 372 [M+H].

Example 12: 4-[4-(4-Fluorophenyl)-5-pyridin-2-yl-1-imidazol-2-yl)phenylamine The title compound was prepared by tin(II)chloride reduction of 4-[4-(4-fluorophenyl)-2-(4-nitrophenyl)-1H-imidazol-5-yl]-pyridine (Example 11). (ESMS): 342. [M+H].

Example 13: 4-(4-Benzo[1,3]dioxol-5-yl-5-pyridin-2-yl-1H-imidazol-2-yl)phenyl]methanol Methyl 4-(4-benzo[1,3]-dioxol-5-yl-4-pyridin-2-yl) benzoate (204 mg; 0.5 mmol) was dissolved in dry tetrahydrofuran (50 ml) under argon and treated dropwise with a solution of lithium hydride in tetrahydrofuran (1M; 1 ml; 1 mmol). After 1 h, more lithium aluminium hydride solution (1 ml) was added and the resulting mixture stirred until tlc examination showed no starting material remaining. Saturated aq. ammonium chloride solution was added, followed by ethyl acetate and the phases were separated. The organic phase was washed with water (×2), saturated brine, dried (MgSO$_4$) and evaporated to dryness under reduced pressure. Trituration of the residue under 60–80° petroleum ether gave a white solid, which was collected by filtration, washed with 60–80° petroleum ether and dried under reduced pressure (103 mg; 54%). $^1$H NMR (250 MHz, CDCl$_3$) δ: 2.10–2.80 (1H, br, exchangeable), 4.73 (2H, s), 6.02 (2H, s), 6.94 (1H, d, J=8 Hz), 7.08–7.18 (3H, m), 7.41 (2H, d, J=8 Hz), 7.53 (2H, brm), 7.92 (2H, d, J=8 Hz), 8.53 (1H, d, J=5 Hz); (ESMS) (M+H)$^+$=372.4.

Example 14: 4-(4-Benzo[1,3]dioxol-5-yl-5-pyridin-2-yl-1H-imidazol-2-yl)benzamide 4-(4-Benzo[1,3]dioxol-5-yl-5-pyridin-2-yl-1H-imidazol-2-yl)benzoyl chloride hydrochloride (100 mg; 0.23 mmol) was suspended in tetrahydrofuran (5 ml) and treated with 0.88 aq. ammonia solution (1 ml) and the resulting mixture stirred at ambient temperature. The title compound (42 mg; 48%) was obtained as a brown powder and collected by filtration, washed with water and dried at 40° C. under reduced pressure. $^1$H NMR (250 MHz, CDCl$_3$) δ: 5.50–6.40 (2H, br, exchangeable), 6.03 (2H, s), 6.90 (1H, d, J=8 Hz), 7.15 (3H, m), 7.55 (2H, brm), 7.89 (2H, d, J=8 Hz), 8.06 (2H, d, J=8 Hz), 8.54 (1H, brd); (ESMS) (M+H)$^+$=385.4.

Example 15: 4-[4-(2,3-Dihydro-benzo[1,4]dioxin-6-yl)-5-pyridin-2-yl-1H-imidazol-2-yl]-benzonitrile Prepared according to the method of Example 2 from 4-[4-(2,3-dihydro-benzo[1,4]dioxin-6-yl)-1-hydroxy-5-pyridin-2-yl-1H-imidazol-2-yl]-benzonitrile. $^1$H NMR (250 MHz, CDCl$_3$) δ: 4.32 (4H, brs), 6.94 (1H, d, J=8.2 Hz), 7.03–7.26 (4H, m), 7.59 (2H, br. s), 7.72 (2H, d, J=8.3 Hz), 8.07 (2H, d, J=8.3 Hz), 8.53 (1H, br. d J=4.6Hz); m/z (API$^+$): 381.1 (MH$^+$).

Example 16: 4-[4-(2,3-Dihydro-benzo[1,4]dioxin-6-yl)-5-pyridin-2-yl-1H-imidazol-2-yl]-benzamide 4-[4-(2,3-Dihydro-benzo[1,4]dioxin-6-yl)-5-pyridin-2-yl-1H-imidazol-2-yl]benzonitrile (1 g) was dissolved in methanol (200 ml). Potassium carbonate was added (1 g) and the resulting suspension treated dropwise with an aqueous hydrogen peroxide solution (10 ml of 30% w/v solution) at 0° C. The suspension was stirred at room temperature for 18 hours then cautiously poured into saturated sodium hydrogen sulfite solution (200 ml) at 0° C. The mixture was tested for the presence of oxidant (starch-iodide test strips) before organic solvent removal by rotary evaporation under reduced pressure. The crude product was digested in ethyl acetate (200 ml). The ethyl acetate layer was dried (MgSO$_4$) and evaporated to dryness under reduced pressure. The title compound was isolated by silica gel column chromatography (using a 1:9:190 ammonia:methanol:dichloromethane solution as eluent) as a beige solid (153 mg, 15%). $^1$H NMR (250 MHz, CDCl$_3$) δ: 4.26 (4H, brs), 6.05 (1H, brs), 6.60 (1H, brs), 6.87 (1 H, brd, J=7. 7 Hz) 7.0–7.25 (3H, 7.53 (2H, d, J=3.7 Hz), 7.76 (2H, d, J=8.2 Hz), 7.95 (2H, d, J=8.2 Hz), 8.47 (1H, d, J=4.6 Hz); m/z (ESMS): 399 (MH$^+$).

Example 17: 4-[4-(2,3-Dihydro-benzofuran-6-yl)-5-pyridin-2-yl-1H-imidazol-2-yl]-benzamide Prepared according to the method of Example 14 from 4-[4-(2,3-dihydro-benzofuran-6-yl)-5-pyridin-2-yl-1H-imidazol-2-yl]-benzonitrile which was prepared from 4-[4-(2,3-dihydro-benzofuran-6-yl)-1-hydroxy-5-pyridin-2-yl-1H-imidazol-2-yl]-benzonitrile according to the method of Example 2. $^1$H NMR (250 MHz, CDCl$_3$) δ: 3.27 (2H, brt, J=8.5 Hz), 4.63 (2H, brt, J=8.5 Hz), 5.50–5.90 (1H, brs), 6.05–6.35 (1H, brs), 7.08–7.20 (3H, m), 7.18–7.30 (3H, m) 7.56 (2H, brs), 8.86 (2H, d, J=8.3 Hz), 8.04 (2H, d, J=8.3 Hz), 8.54 (1H, brd, J=4.5 Hz); m/z (ESMS): 383.5 (MH$^+$).

Example 18: 3-(4-Benzo[1,3]dioxol-5-yl-5-pyridin-2-yl-1H-imidazol-2-yl)benzonitrile Prepared according to the method of Example 2 from 3-(4-benzo[1,3]dioxol-5-yl-1-hydroxy-5-pyridin-2-yl-1H-imidazol-2-yl)-benzonitrile. $^1$H NMR (250 MHz, CDCl$_3$) δ: 6.03 (s, 2H), 6.90 (d, 1H, J=8.37 Hz), 7.15 (m, 3H), 7.57 (m, 4H), 8.16 (d, 1H, J=7.90 Hz), 8.23 (s, 1H), 8.51 (d, 1H); m/z (AP+): 367 (M+H)$^+$, 368 (M+2H)$^+$.

Example 19: 4-[4-(2,3-Dihydro-benzofuran-6-yl)-5-pyridin-2-yl-1H-imidazol-2-yl]-benzonitrile The title compound was prepared using the procedure of Example 1 except using 1-(2,3-Dihydro-benzofuran-6-yl)-2-pyridin-2-yl-ethane-1,2-dione oxime and 4-cyanobenzaldehyde. m/z (ESMS): 365 [M+H].

Example 20: 4-[4-(2,3-Dihydro-benzofuran-6-yl)-5-pyridin-2-yl-1H-imidazol-2-yl]-benzamide Prepared according to the method of Example 16 from 4-[4-(2,3-dihydro-benzofuran-6-yl)-5-pyridin-2-yl-1H-imidazol-2-yl]-benzonitrile which was prepared from 4-[4-(2,3-dihydrobenzofuran-6-yl)-1-hydroxy-5-pyridin-2-yl-1H-imidazol-2-yl]-benzonitrile according to the method of Example 2. $^1$H NMR (250 MHz, CDCl$_3$) δ: 3.27 (2H, brt, J=8.5 Hz), 4.63 (2H, brt, J=8.5 Hz), 5.50–5.90 (1H, brs), 6.05–6.35 (1H, brs), 7.08–7.20 (3H, m), 7.18–7.30 (3H, m) 7.56 (2H, brs), 8.86 (2H, d, J=8.3 Hz), 8.04 (2H, d, J=8.3 Hz), 8.54 (1H, brd, J=4.5 Hz); m/z (ESMS): 383.5 (MH$^+$).

Example 21: 3-(4-Benzo[1,3]dioxol-5-yl-5-pyridin-2-yl-1H-imidazol-2-yl)benzoic acid 3-(4-Benzo[1,3]dioxol-5-yl-5-pyridin-2-yl-1H-imidazol-2-yl)-benzonitrile (600 mg, 1.64 mmol) was dissolved in ethanol (20 ml) 2M aq. NaOH (50 ml) was added and the mixture heated at reflux overnight. On cooling, the solution was acidified to pH 1 with 5M aq. HCl and the precipitate collected by filtration, washed with water then diethyl ether and dried to afford a yellow/green solid. $^1$H NMR (250 MHz, DMSO) δ 6.06 (s, 2H), 6.97 (d, 1H), 7.20 (dd, 3H), 7.57 (t, 1H), 7.80 (t, 1H), 7.90 (d, 1H), 8.30 (s, 2H), 8.74 (s, 1H), m/z (AP+): 385 (M+H)$^+$ 386 (M+2H)$^+$.

Example 22: 4-[4-(4-Methoxyphenyl)-5-(2-pyridyl)-1H-imidazol-2-yl]benzonitrile

The title compound was prepared using the procedure of Example 1 except using 1-(4-methoxyphenyl)2-pyridin-2-yl-ethane-1,2-dione oxime and 4-cyanobenzaldehyde. m/z (ESMS): 353 [M+H].

Example 23: 4-[4-(2,2-Difluoro-benzo[1,3]dioxol-5-yl)-5-pyridin-2-yl-1H-imidazol-2-yl]-benzamide Prepared according to the method of Example 16 except using 4-[4-(2,2-difluoro-benzo[1,3]dioxol-5-yl)-5-pyridin-2-yl-1H-imidazol-2-yl]-benzonitrile which was prepared according to the method of Example 2. m/z (ESMS): 421 [M+H].

Example 24: 4-[4-(2,3-Dihydro-benzo[1,4]dioxin-6-yl)-1-methyl-5-pyridin-2-yl-1H-imidazol-2-yl] benzamide The title compound was prepared using the procedure outlined in N. J. Liverton et al, *J. Med Chem.* 1999, 42, 2180–2190 via alkylation of Example 15 followed by nitrile hydrolysis as described in Example 16. $^1$H NMR (250MHz, CDCl$_3$) δ: 3.74 (3H, s), 4.24 (4H, s), 5.30 (1H, brs), 6.25 (1H, brs), 6.74 (2H, d, J=8Hz), 6.95 (1H, dd, J=1,8 Hz), 7.06 (1H, d, J=1 Hz), 7.26 (1H, m), 7.38 (1H, d, J=8 Hz), 7.66 (1H, m), 7.83, (2H, d, J=7 Hz), 7.91 (2H, d, J=7 Hz), 8.77 (1H, d, J=7 Hz); m/z (AP+): 413 (M+H)$^+$.

Example 25: 4-[5-(2,3-Dihydro-benzo[1,4]dioxin-6-yl)-1-methyl-4-pyridin-2-yl-1H-imidazol-2-yl] benzamide The title compound was prepared using the procedure outlined in N. J. Liverton et al, *J. Med Chem.* 1999, 42, 2180–2190 via alkylation of Example 15 followed by nitrile hydrolysis as described in Example 16. $^1$H NMR (250 MHz, DMSO) δ: 3.52 (3H, s), 4.29 (4H, s), 6.92 (2H, s), 6.96 (1H, s), 7.14 (1H, m), 7.48 (1H, s), 7.81 (2H, m), 7.83 (2H, d, J=7 Hz), 8.02 (2H, d, J=7 Hz), 8.10 (1H, s), 8.34 (1H, d, J=2 Hz); m/z (AP+): 413 (M+H)$^+$.

Example 26: 4-(5-Benzo[1,3]dioxol-5-yl-4-pyridin-2-yl-oxazol-2-yl)benzonitrile

N-(2-Benzo[1,3]dioxol-5-yl-2-oxo-1-pyridin-2-yl-ethyl) 4-cyano-benzamide (0.1 g, 0.26 mmol) was dissolved in neat thionyl chloride (10 ml) and heated at reflux temperature for 2 hours. The cooled solution was cautiously added dropwise to a concentrated sodium hydroxide-ice mixture. The crude product was extracted into dichloromethane and purified using hexane-ethylacetate (1:1) as eluent to give the title compound (9 mg, 9%). $^1$H NMR (CDCl$_3$) δ: 6.06 (2H, s), 6.84–6.99 (2H, m), 7.27–7.31 (1H, m), 7.86 (2H, d, J=7 Hz), 8.00 (2H, d, J=7 Hz), 8.04 (1H, s), 8.23 (1H, dd, J=7 and 1 Hz), 8.42 (1H, d, J=7 Hz), 8.65 (1H, dd, J=7 and 1 Hz); m/z (API) 368 (M+H$^+$).

Example 27: 4-(5-Benzo[1,3]dioxol-5-yl-4-pyridin-2-yl-oxazol-2-yl)benzamide

Prepared from 4-(5-benzo[1,3]dioxol-5-yl-4-pyridin-2-yl-oxazol-2-yl)-benzonitrile using hydrogen peroxide and methanolic potassium carbonate according to Example 16 and isolated in 44% yield. $^1$H NMR (DMSO) δ: 6.15 (2H, s), 7.08–7.16 (2H, m), 7.45–7.54 (2H, m), 7.95–7.99 (1H, m), 8.02 (1H, br. s), 8.08 (1H, br. s), 8.12–8.15 (2H, m), 8.22 (1H, dd, J=7 and 1 Hz), 8.48 (1H, d, J=8 Hz), 8.74 (1H, d, J=8 Hz); m/z (API) 386 (M+H$^+$).

Example 28: 4(4-Benzo[1,3]dioxol-5-yl-5-pyridin-2-yl-1H-pyrrol-2-yl)benzamide 4-(3-Benzo[1,3]dioxol-5-yl-4-oxo4-pyridin-2-ylbutanoyl)benzamide (1.69 g; 4.2 mmol) and ammonium acetate (2.1 g; 27.3 mmol) were reacted together according to the method described in *Bioorg. Med. Chem. Letters*, 1998, 8, 2689–2694. The title compound was isolated as a brown powder from methanol (126 mg; 8%). $^1$H NMR (DMSO) δ: 6.04 (2H, s), 6.82–6.93 (4H, m), 7.18–7.32 (3H, m), 7.63–7.74 (1H, m), 7.86–7.96 (5H, m), 8.61 (1H, d, J=4 Hz), 11.63 (1H, brs); m/z (LCMS): 383.9 (M+H)$^+$.

INTERMEDIATES

Preparation 1: 1-(2,3-Dihydro-benzo[1,4]dioxin-6-yl)-2-pyridin-2-yl-ethanol

Diisopropylamine (18.8 ml, 1.1 equiv) was dissolved in dry THF (200 ml) under argon and cooled to −78° C. n-Butyl lithium in hexane (2.5M→53.6 ml, 1.1 equiv.) was added, followed by a dropwise addition of 2-methyl pyridine (12.0 ml, 1 equiv). The reaction mixture was stirred for 15 minutes at −78° C. and was then treated with 1,4-benzodioxan-6-carboxaldehyde (20 g, 121.8 mmol) in dry THF (50 ml). The reaction mixture was stirred at −78° C. for 30 min then allowed to return to room temperature overnight.

Excess saturated aqueous ammonium chloride was added to the mixture followed by 200 ml EtOAc. The organic phase was separated and washed with 2M NaOH (2×150 ml), H$_2$O (3×100 ml), brine (100 ml) dried (MgSO$_4$) and evaporated to dryness. (31.6 g, quantitative). $^1$H NMR (400 MHz, CDCl$_3$) δ: 3.07 (d, 2H), 4.20 (s, 4H), 5.03 (m, 1H), 5.57 (brs, 1H), 6.81 (d, 1H), 6.85 (d, 1H), 6.94 (s, 1H), 7.09–7.14 (m, 2H), 7.57 (t, 1H), 8.46 (s, 1H). m/z (ES+): 258 (M+H)$^+$, 240 (M−OH)$^+$.

Preparation 2: 4-(4-Benzo[1,3]dioxol-5-yl-5-pyridin-2-yl-1H-imidazol-2-yl)benzoyl chloride hydrochloride 4-(4-Benzo[1,3]dioxol-5-yl-5-pyridin-2-yl-1H-imidazol-2-yl)benzoic acid (379 mg; 0.98 mmol) was suspended in dry dichloromethane (20 ml) under argon and treated sequentially with oxalyl chloride (0.1 ml) then N,N-dimethylformamide (1 drop). The mixture was stirred at ambient temperature for 1 h. More oxalyl chloride (2×0.1 ml) was added at 1 h and 2 h and the mixture stirred at ambient temperature for 5 h. Volatiles were removed under reduced pressure to give the title compound as an orange powder: m/z (methyl ester; API): 400.3 (M+H)$^+$.

Preparation 3: 2,3-Dihydro-benzofuran-6-ol

6-Hydroxy-2H-benzofuran-3-one (3 g) was suspended in anhydrous tetrahydrofuran under an argon atmosphere and cooled to 0° C. Lithium aluminium hydride (20 ml of a 1M solution in tetrahydrofuran) was added dropwise over 10 min and the reaction allowed to reach room temperature over 2 hours. The reaction was cooled to 0° C. and treated dropwise with saturated ammonium chloride solution. Ethyl acetate (200 ml) was added and the mixture filtered through Celite. The ethyl acetate layer was separated, dried (MgSO$_4$) and evaporated to dryness under reduced pressure. The resulting mixture of 2,3-dihydro-benzofuran-3,6-diol and benzofuran-6-ol (approximately 1:1 by 250 MHz $^1$H NMR) was dissolved in a mixture of hydrochloric acid (200 ml, 5M aqueous solution) and methanol (300 ml) and palladium hydroxide (0.5 g) added. The mixture was stirred under a hydrogen atmosphere for 3 hours then filtered through Celite. The organics were removed by evaporation under reduced pressure and the resulting solution neutralised with concentrated anmmonia solution. The product was extracted into dichloromethane. The dichloromethane solution was dried (MgSO$_4$) and evaporated to dryness under reduced pressure to yield the title compound (2.5 g, 92%). $^1$H NMR (250 MHz, CDCl$_3$) δ: 3.11 (2H, t, J=8.4 Hz), 4.57 (2H, t, J=8.4 Hz), 6.27–6.34 (2H, m), 6.92–7.02 (1H, m); m/z (API+): 139.1 (M+3H$^+$).

Preparation 4: Trifluoro-methanesulfonic acid 2,3-dihydro-benzofuran-6-yl ester 2,3-Dihydro-benzofuran-6-ol (2.5 g) was dissolved in anhydrous dichloromethane under an argon atmosphere. Triethylamine (3.5 ml) was added and the reaction cooled to 0° C. A solution of trifluoromethane sulfonic anhydride (3.1 ml) in dichloromethane (10 ml) was added drop-wise over 1 minute. After 2 hours the reaction was quenched by the addition of a saturated sodium bicarbonate solution (50 ml). The reaction mixture was partitioned between water (100 ml) and dichloromethane (200 ml). The dichloromethane layer was separated, dried (MgSO$_4$) and evaporated to dryness under reduced pressure. The resulting residue was isolated in quantitative yield by silica gel column chromatography (using 1:3 ethyl acetate:hexane as eluent). $^1$H NMR (250 MHz, CDCl$_3$) δ: 3.22 (2H, t, J=8.4 Hz), 4.66 (2H, t, J=8.4 Hz), 6.68 (1H, d, J=1 Hz), 6.74 (1H, dd, J=8 and 1 Hz), 7.20 (1H, d, J=8 Hz); m/z (API$^+$): 271(M+3H$^+$).

Preparation 5: 2,3-Dihydro-benzofuran-6-carboxylic acid

Palladium bis(triphenylphosphine) dibromide (3 g) was added to a degassed methanolic solution (30 ml) of trifluoro-methanesulfonic acid 2,3-dihydro benzofuran-6-yl ester (5 g) and tributylamine (5 ml). The mixture was charged with carbon monoxide at 40 psi in a Berghoff pressure vessel then heated at 100° C. for 72 hours. The resulting methanolic solution of 2,3-dihydro-benzofuran-6-carboxylic acid methyl ester was treated with sodium hydroxide solution (50 ml of 2M aqueous solution) and stirred at room temperature for 18 hours. The reaction mixture was acidified to pH 1 with hydrochloric acid (5M aqueous solution) and extracted with ethyl acetate (300 ml). The ethyl acetate layer was separated and the product extracted into saturated sodium bicarbonate solution (200 ml). The sodium bicarbonate solution was acidified to pH 1 with hydrochloric acid (5M aqueous solution) and the resulting precipitate dissolved in ethyl acetate. The ethyl acetate layer was separated, dried (MgSO$_4$) and evaporated to dryness under reduced pressure to yield the title compound (0.6 g, 20%). $^1$H NMR (250 MHz, CD$_3$OD) δ: 3.20 (2H, t, J=8.6 Hz), 4.54 (2H, t, J=8.6 Hz), 7.23 (1H, d, J=8 Hz), 7.25 (1H, brs), 7.49(1H, dd, J=8 and 1 Hz).

Preparation 6: 2-Amino-1-benzo[1,3]dioxol-5-yl-2-pyridin-2-yl-ethanone dihydrochloride 1-Benzo[1,3]dioxol-5-yl-2-pyridin-2-yl-ethane-1,2-dione 2-oxime (2 g, 7.75 mmol) was dissolved in ethanol (100 ml) and hydrochloric acid (2 ml of a 36% solution in water) was added. Palladium on charcoal catalyst (0.5 g) was added and the reaction mixture was stirred under a positive pressure of hydrogen for 1.5 hours. The catalyst was removed by filtration through Kieselguhr and the resulting filtrate evaporated to dryness under reduced pressure. Trituration under anhydrous diethyl ether gave the title compound as a pale yellow solid (1.5 g, 59%); m/z (API) 257 (M+H$^+$, 100%).

Preparation 7: N-(2-Benzo[1,3]dioxol-5-yl-2-oxo-1-pyridin-2-yl-ethyl)4-cyano-benzamide 2-Amino-1-benzo[1,3]dioxol-5-yl-2-pyridin-2-yl-ethanone dihydrochloride (1 g, 3 mmol) was added to a stirring solution of 4-cyano-benzoyl chloride (0.459 g, 3 mmol) in dichloromethane (10 ml). Triethylamine (2 ml, 14 mmol) was added dropwise and the reaction was stirred at ambient temperature for 18 hours. Water was (50 ml) added the organics were extracted into dichloromethane. Chromatographic purification using a dichloromethane solution of ammonia in methanol (0.5% c. ammonia: 4.5% methanol: 95% dichloromethane) yielded the title compound as a pale yellow oil (0.9 g, 76%); m/z (API) 386 (M+H$^+$, 100%).

Preparation 8: 4-((E/Z)-3-Benzo[1,3]dioxol-5ylallanoyl)benzamide.

4-Acetylbenzamide (1.3 g; 8 mmol) was dissolved in methanol (50 ml) and piperonal (1.19 g; 8 mmol) added, followed by 2M aqueous sodium hydroxide solution (6 ml; 12 mmol). The resulting mixture was left to stand at ambient temperature for 72 h. The crystalline precipitate was collected by filtration, washed well with water and dried at 40° C. under reduced pressure (1.51 g; 64%); $v_{max}$ (CH$_2$Cl$_2$) 1682, 1651, 1424 and 1265 cm$^{-1}$; $^1$H NMR (DMSO) δ: 6.08 (2H, s), 6.96 (1H, d, J=8 Hz), 7.30 and 7.33 (1H, dd, J=8 and 1 Hz), 7.54 (1H, br, exchangeable), 7.65 (1H, d, J=1 Hz), 7.67 (1H, d, J=15 Hz), 7.82 (1H, d, J=15 Hz), 7.98 (2H, d, J=8 Hz), 8.15–8.18 (3H, brd); m/z (API): 296 (M+H)$^+$.

Preparation 9: 4-(3-Benzo[1,3]dioxol-5-yl-4-oxo-4-pyridin-2-ylbutanoyl)benzamide.

4-((E/Z)-3-benzo[1,3]dioxol-5-ylallanoyl)benzamide (1.47 g; 4.98 mmol), pyridine-2-carboxaldehyde (533 mg; 4.98 mmol) and sodium cyanide (24 mg; 10 mol %) were mixed together in N,N-dimethylformamide (30 ml) and the resulting mixture heated at reflux for 18 h. The reaction mixture was cooled to room temperature and poured into water with vigorous stirring then extracted with ethyl acetate. The combined organic extracts were washed with water, saturated brine, dried (MgSO$_4$) and evaporated to dryness under reduced pressure to give the title compound as a black foam (1.69 g; 84%); m/z (API); 403.1 (M+H)$^+$.

Biological Data

The biological activity of the compounds of the invention may be assessed using the following assays:

Method for evaluating ALK5 Kinase Phosphorylation of Smad3

Basic Flash-Plates (NEN Life Sciences) were coated by pipetting 100 micro liter of 0.1 molar sodium bicarbonate (pH 7.6), containing 150 nanograms of the fusion protein glutathion-S-transferase-smad3/100 micro liter of coating buffer. Plates were covered and incubated at room temperature for 10–24 hours. Then the plates were washed 2 times with 200 micro liter of coating buffer (0.1 molar sodium bicarbonate) and allowed to air dry for 2–4 hours.

For the phosphorylation reaction each well received 90 microliter containing 50 millimolar HEPES buffer (pH 7.4); 5 millimolar MgCl$_2$; 1 millimolar CaCl$_2$; 1 millimolar dithiothreitol; 100 micromolar guanosine triphosphate; 0.5 micro Ci/well gamma$^{33}$P-adenosine triphosphate (NEN Life Sciences) and 400 nanograms of a fusion protein of glutathion -S-transferase at the N-terminal end of the kinase domain of ALK5 (GST-ALK5). Background counts were measured by not adding any GST-ALK5. Inhibitors of ALK5 were evaluated by determining the activity of the enzyme in the presence of various compounds. Plates were incubated for 3 hours at 30° C. After incubation the assay buffer was removed by aspiration and the wells were washed 3 times with 200 microliter cold 10 millimolar sodium pyrophosphate in phosphate buffered saline. The last wash was aspirated and blotted plate dry. Plate was then counted on a Packard TopCount.

Inhibition of Matrix Markers: Western Blot Protocol

Data confirming activity in the enzyme assay was obtained as follows.

Cells were grown to near confluence in flasks, starved overnight and treated with TGF-beta and compounds. Cells were washed at 24 or 48 hours after treatment with ice cold phosphate buffered saline, then 500 microliter of 2x loading buffer was added to plate and cells were scraped and collected in microcentrifuge tube. (2x loading buffer: 100 mM Tris-Cl, pH6.8, 4% sodium dodecyl sulfate, 0.2% bromophenol blue, 20% glycerol, 5% beta-mercaptoethanol). Cells were lysed in tube and vortexed. Sample was boiled for 10 minutes. 20 microliters of sample was loaded on 7.5% polyacrylamide gel (BioRad) and electrophoresed.

Size fractionated proteins in gel were transferred to nitrocellulose membrane by semidry blotting. Membrane was blocked overnight with 5% powdered milk in phosphate buffer saline (PBS) and 0.05% Tween-20 at 4 degrees C. After 3 washes with PBS/Tween membranes were incubated with primary antibody for 4 hours at room temperature. After three washes with PBS/Tween membrane was incubated with secondary antibody for 1 hour at room temperature. Finally, a signal was visualized with ECL detection kit from Amersham.

The compounds of this invention generally show ALK5 receptor modulator activity having IC$_{50}$ values in the range of 0.0001 to 10 μM.

What is claimed is:

1. A compound of formula (I) or a pharmaceutically acceptable salt thereof:

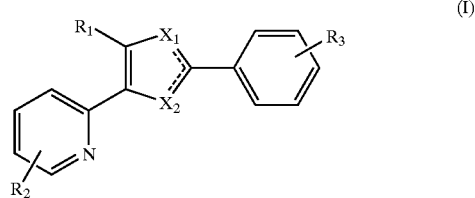

(I)

wherein R$_1$ is naphthyl, anthracenyl, or phenyl optionally substituted with one or more substituents selected from the group consisting of halo, C$_{1-6}$alkoxy, C$_{1-6}$alkylthio, C$_{1-6}$alkyl, —O—(CH$_2$)$_n$—Ph, —S—(CH$_2$)$_n$—Ph, cyano, phenyl, and CO$_2$R, wherein R is hydrogen or C$_{1-6}$alkyl and n is 0, 1, 2 or 3; or R$_1$ is phenyl fused with an aromatic or non-aromatic cyclic ring of 5–7 members wherein said cyclic ring optionally contains up to two heteroatoms, independently selected from N, O and S;

R$_2$ is H, NH(CH$_2$)$_n$—Ph or NH—C$_{1-6}$alkyl, wherein n is 0, 1, 2 or 3;

R$_3$ is CO$_2$H, CONH$_2$, CN, NO$_2$, C$_{1-6}$alkylthio, —SO$_2$—C$_{1-6}$alkyl, C$_{1-6}$alkoxy, SONH$_2$, CONHOH, NH$_2$, CHO, CH$_2$OH, CH$_2$NH$_2$, or CO$_2$R, wherein R is hydrogen or C$_{1-6}$alkyl; and one of X$_1$ and X$_2$ is N or CR', and the other is NR' or CHR' wherein R' is hydrogen, OH, C$_{1-6}$alkyl, or C$_{3-7}$cycloalkyl; or when one of X$_1$ and X$_2$ is N or CR' then the other may be S or O.

2. A compound according to claim 1 wherein R$_1$ is phenyl optionally substituted with one or more substituents selected from the group consisting of halo, C$_{1-6}$alkoxy, C$_{1-6}$alkylthio, and phenyl; or R$_1$ is phenyl fused with an aromatic or non-aromatic cyclic ring of 5–7 members wherein said cyclic ring optionally contains up to two heteroatoms, independently selected from N, O and S.

3. A compound according to claim 1 wherein R$_2$ is positioned ortho to the nitrogen of the pyridyl ring.

4. A compound according to claim 1 wherein R$_3$ is CO$_2$H, CONH$_2$, CN, NO$_2$, SONH$_2$, CONHOH, NH$_2$, CHO, CH$_2$OH or CH$_2$NH$_2$.

5. A compound according to claim 1 wherein one of X$_1$ and X$_2$ is N or CR', and the other is NR' or CHR' wherein R' is hydrogen, C$_{1-6}$alkyl, or C$_{3-7}$cycloalkyl, provided that at least one of X$_1$ and X$_2$ is N or NR'; or one of X$_1$ and X$_2$ is N and the other is O.

6. A compound according to claim 5 wherein one of X$_1$ and X$_2$ is N and the other is NR'.

7. A compound according to claim 1 wherein each R' is hydrogen.

8. A compound according to claim 1 selected from the group comprising:

4-[4-(4-Fluorophenyl)-5-(2-pyridyl)-1-hydroxy-1H-imidazol-2-yl]benzonitrile;

4-[4-(4-Fluorophenyl)-5-(2-pyridyl)-1H-imidazol-2-yl]benzonitrile;

4-[4-(4-Fluorophenyl)-5-(2-pyridyl)-1H-imidazol-2-yl]benzoic acid;

Methyl 4-[4-(4-fluorophenyl)-5-(2-pyridyl)-1H-imidazol-2-yl]benzoate;

Ethyl 4-[4-(4-fluorophenyl)-5-(2-pyridyl)-1H-imidazol-2-yl]benzoate;

4-(4-Benzo[1,3]dioxol-5-yl-1-hydroxy-5-pyridin-2-yl-1H-imidazol-2-yl)benzonitrile;

4-(4-Benzo[1,3]dioxol-5-yl-5-pyridin-2-yl-1H-imidazol-2-yl)benzonitrile;

4-(4-Benzo[1,3]dioxol-5-yl-5-pyridin-2-yl-1H-imidazol-2-yl)benzoic acid;

2-[4-Benzo[1,3]dioxol-5-yl-2-(4-nitrophenyl)-1H-imidazol-5-yl]pyridine;

3-(4-Benzo[1,3]dioxol-5-yl-5-pyridin-2-yl-1H-imidazol-2-yl)phenylamine;

4-[4-(4-Fluorophenyl)-2-(4-nitrophenyl)-1H-imidazol-5-yl]pyridine;

4-[4-(4-Fluorophenyl)-5-pyridin-2-yl-1H-imidazol-2-yl)phenylamine;

4-(4-Benzo[1,3]dioxol-5-yl-5-pyridin-2-yl-1H-imidazol-2-yl)phenyl]methanol;

4-(4-Benzo[1,3]dioxol-5-yl-5-pyridin-2-yl-1H-imidazol-2-yl)benzamide;

4-[4-(2,3-Dihydro-benzo[1,4]dioxin-6-yl)-5-pyridin-2-yl-1H-imidazol-2-yl]-benzonitrile;

4-[4-(2,3-Dihydro-benzo[1,4]dioxin-6-yl)-5-pyridin-2-yl-1H-imidazol-2-yl]benzamide;

4-[4-(2,3-Dihydro-benzofuran-5-yl)-5-pyridin-2-yl-1H-imidazol-2-yl]benzamide;

3-[4-Benzo[1,3]dioxol-5-yl-5-pyridin-2-yl-1H-imidazol-2-yl)benzonitrile;

4-[4-(2,3-Dihydro-benzofuran-6-yl)-5-pyridin-2-yl-1H-imidazol-2-yl]benzonitrile;

4-[4-(2,3-Dihydro-benzofuran-6-yl)-5-pyridin-2-yl-1H-imidazol-2-yl]benzamide;

3-(4-Benzo[1,3]dioxol-5-yl-5-pyridin-2-yl-1H-imidazol-2-yl)benzoic acid;

4-[4-(4-Methoxyphenyl)-5-(2-pyridyl)-1H-imidazol-2yl]benzonitrile;

4-[4-(2,2-Difluoro-benzo[1,3]dioxol-5-yl)-5-pyridin-2-yl-1H-imidazol-2-yl]benzamide;

4-[4-(2,3-Dihydro-benzo[1,4]dioxin-6-yl)-1-methyl-5-pyridin-2-yl-1H-imidazol-2-yl]benzamide;

4-[5-(2,3-Dihydro-benzo[1,4]dioxin-6-yl)-1-methyl-4-pyridin-2-yl-1H-imidazol-2-yl]benzamide;

4-(5-Benzo[1,3]dioxol-5-yl-4-pyridin-2-yl-oxazol-2-yl)benzonitrile;

4-(5-Benzo[1,3]dioxol-5-yl-4-pyridin-2-yl-oxazol-2-yl)benzamide; and 4-(4-Benzo[1,3]dioxol-5-yl-5-pyridin-2-yl-1H-pyrrol-2-yl)benzamide; or a pharmaceutically acceptable salt thereof.

9. A pharmaceutical composition comprising a compound according claim 1 or a pharmaceutically acceptable salt thereof, and a pharmaceutically acceptable carrier or diluent.

10. A method of inhibiting the TGF-β signaling pathway in mammals, comprising administering to a mammal in need of such treatment, a therapeutically effective amount of a compound according to claim 1, or a pharmaceutically acceptable salt thereof.

11. A method for treating a disease selected from chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, trophic conditions, atherosclerosis, peritoneal and sub-dermal adhesion, any disease wherein fibrosis is a major component, and restenosis, comprising administering to a mammal in need of such treatment, a therapeutically effective amount of a compound according to claim 1, or a pharmaceutically acceptable salt thereof.

12. A method for inhibiting matrix formation in mammals, comprising administering to a mammal, a therapeutically effective amount of a compound according to claim 1, or a pharmaceutically acceptable salt thereof.

* * * * *